United States Patent [19]

VandenBerg

[11] Patent Number: Plant 6,314

[45] Date of Patent: Sep. 27, 1988

[54] CHRYSANTHEMUM PLANT NAMED BRONZE CHARM

[75] Inventor: Cornelis P. VandenBerg, Salinas, Calif.

[73] Assignee: Yoder Brothers, Inc., Barberton, Ohio

[21] Appl. No.: 920,200

[22] Filed: Oct. 17, 1986

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Bronze Charm particularly characterized by its flat capitulum form; decorative capitulum type; bronze ray floret color; diameter across face of capitulum of up to 11 cm at maturity when grown as a pinched disbudded pot mum; uniform eight week photoperiodic flowering response to short days; medium plant height when grown as a pinched pot mum, and spreading branching pattern.

3 Drawing Sheets

The present invention comprises a new and distinct cultivar of Chrysanthemum, botanically known as *Chrysanthemum morifolium*, and referred to by the cultivar name Bronze Charm.

Bronze Charm, identified as 79I34B04, is a product of a mutation induction program which had the objective of creating new Chrysanthemum cultivars that would expand the color range of an existing cultivar while retaining all other traits.

Bronze Charm was discovered and selected by Cornelis P. VandenBerg on May 17, 1983 in a controlled environment in Salinas, Calif. as one flowering plant within a flowering block established as rooted cuttings from stock plants which had been exposed as unrooted cuttings to an X-ray source of 2200 rads. The irradiated parent was the cultivar Charm, disclosed in U.S. Plant Pat. No. 5,502.

The first act of asexual reproduction of Bronze Charm was accomplished when vegetative cuttings were taken from the initial selection in August of 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Bronze Charm are firmly fixed and are retained through successive generations of asexual reproduction.

Bronze Charm has not been observed under all possible environmental conditions. The phenotype may vary significantly with variations in environment such as temperature, light intensity, and day length.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Bronze Charm, which, in combination, distinguish this Chrysanthemum as a new and distinct cultivar:

1. Flat capitulum form.
2. Decorative capitulum type.
3. Bronze ray floret color.

4. Diameter across face of capitulum up to 11 cm at maturity, when grown as a pinched disbudded pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Spreading branching pattern.

The accompanying photographic drawings show typical inflorescence and leaf characteristics of Bronze Charm, with the colors being as nearly true as possible with illustrations of this type.

Sheet 1 is a color photograph of Bronze Charm grown as a pinched disbudded pot mum.

Sheet 2 is a black and white photograph of three views of the inflorescence of Bronze Charm.

Sheet 3 is a black and white photograph showing the upper and under sides of the leaves of Bronze Charm at three stages of development (mature, intermediate and immature).

Of the commercial cultivars known to the inventor, the most similar in comparison to Bronze Charm is the parent cultivar Charm. All traits of Bronze Charm are similar to those of Charm, except the color of ray florets. The color of the ray florets of Bronze Charm is bronze, as contrasted with the light lavender pink ray florets of Charm.

In the following description, color references are made to The Royal Horticultural Society Colour Chart. The exact color for the corolla of florets of Bronze Charm is not represented in the R.H.S. Colour Chart, and the color values given are those closest to the actual color of Bronze Charm. The color values were determined on plant material grown as a pinched disbudded pot mum in Salinas, Calif. on Mar. 24, 1986.

Classification:

*Botanical.*—*Chrysanthemum morifolium*, Ramat., cv. Bronze Charm.

*Commercial.*—Decorative disbudded pot mum.

INFLORESCENCE

A. Capitulum:

*Form.*—Flat.

*Type.*—Decorative.

*Diameter across face.*—Up to 11 cm at maturity.

B. Corolla of ray florets:

*Color (general tonality from a distance of three meters).*—Bronze.

*Color (upper surface).*—172C to 172D, oxidizing to 168D.

*Color (under surface).*—168D.

*Shape.*—Flat, oblong.

C. Corolla of disc florets:

*Color (mature).*—154B.

*Color (immature).*—149B.

D. Reproductive organs:

*Androecium.*—Present in disc florets only, very few; scant pollen.

*Gynoecium.*—Present in both ray and disc florets.

PLANT

A. General appearance:

*Height.*—Medium; 25 to 35 cm as a pinched disbudded pot mum with 0 to 7 long days after pinch prior to short days and 1 application of 2500 ppm B-9 SP.

*Branching pattern.*—Spreading.

B. Foliage:

*Color (upper surface).*—147B.

*Color (under surface).*—148B.

*Shape.*—Lobed and serrated.

I claim:

1. A new and distinct Chrysanthemum plant named Bronze Charm, as described and illustrated, and particularly characterized as to uniqueness by the combined characteristics of flat capitulum form; decorative capitulum type; bronze ray floret color; diameter across face of capitulum of up to 11 cm at maturity when grown as a pinched disbudded pot mum; uniform eight week photoperiodic flowering response to short days; medium plant height when grown as a pinched pot mum, and spreading branching pattern.

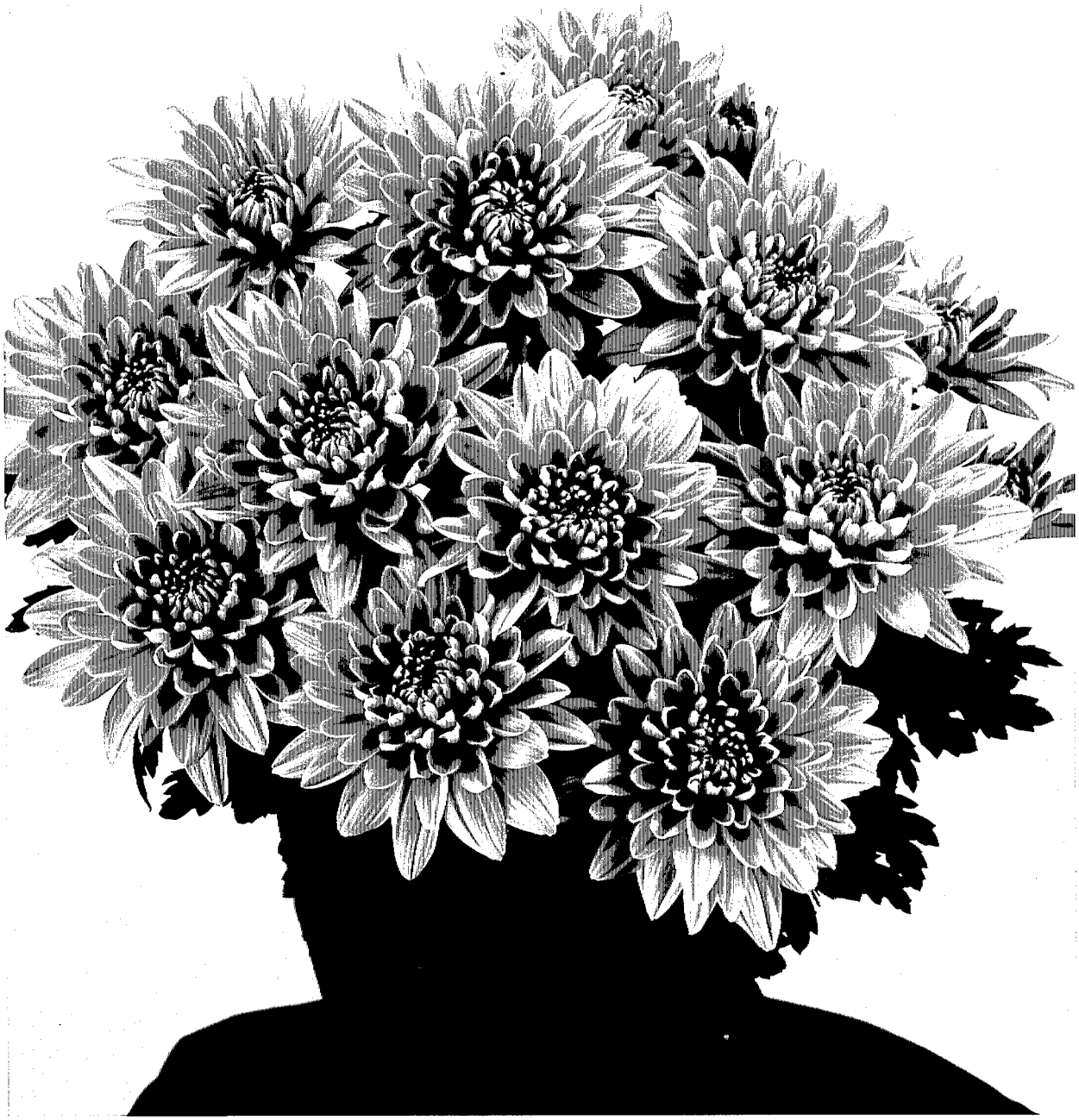

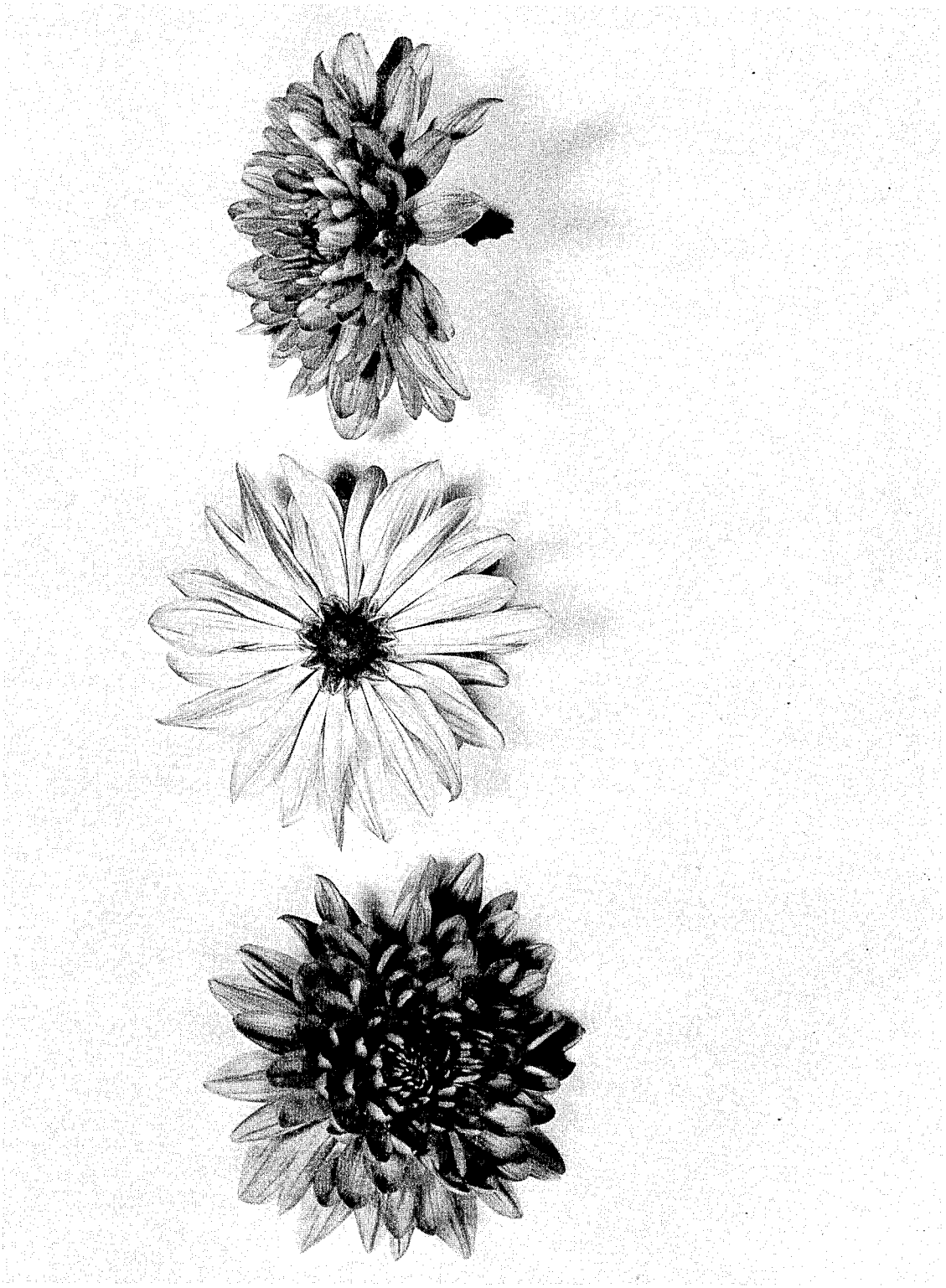

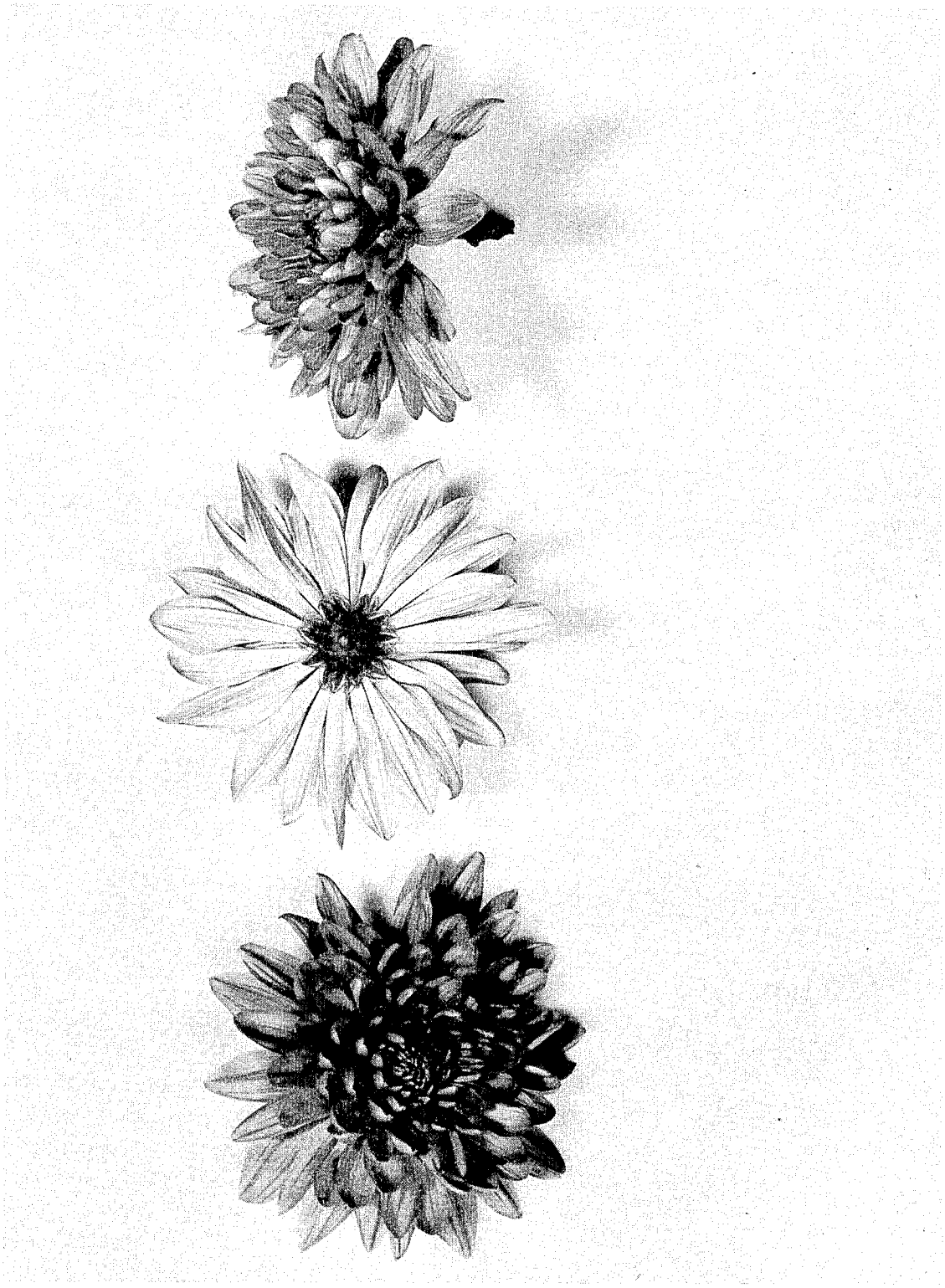

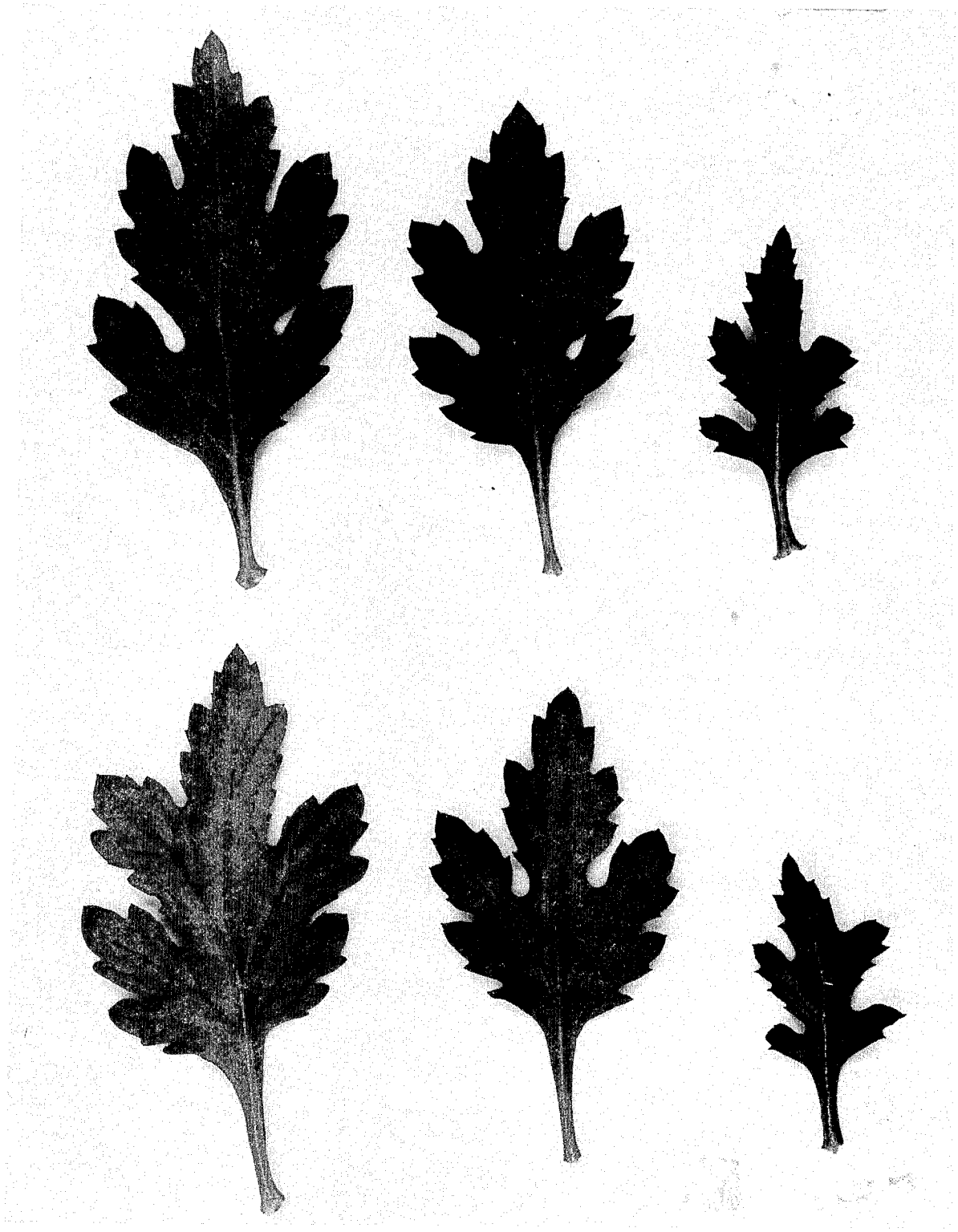

* * * * *